US012753197B2

United States Patent

Che et al.

(10) Patent No.: US 12,753,197 B2
(45) Date of Patent: Oct. 6, 2026

(54) COLOUR TUNABLE LUMINESCENT BIDENTATE PLATINUM (II) COMPLEXES FOR PROBING MISMATCH DNA

(71) Applicant: THE UNIVERSITY OF HONG KONG, Hong Kong (CN)

(72) Inventors: Chi Ming Che, Hong Kong (CN); Ming Zhang, Hainan (CN); Chun Nam Lok, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1197 days.

(21) Appl. No.: 17/754,018

(22) PCT Filed: Sep. 7, 2020

(86) PCT No.: PCT/CN2020/113745

§ 371 (c)(1),
(2) Date: Mar. 21, 2022

(87) PCT Pub. No.: WO2021/052207

PCT Pub. Date: Mar. 25, 2021

(65) Prior Publication Data

US 2023/0212208 A1 Jul. 6, 2023

Related U.S. Application Data

(60) Provisional application No. 62/902,474, filed on Sep. 19, 2019.

(51) Int. Cl.
*C12Q 1/683* (2018.01)
*C07F 15/00* (2006.01)

(52) U.S. Cl.
CPC .......... *C07F 15/0086* (2013.01); *C12Q 1/683* (2013.01)

(58) Field of Classification Search
CPC ........ C12Q 2545/114; C12Q 2563/103; C12Q 1/683
See application file for complete search history.

(56) References Cited

U.S. PATENT DOCUMENTS 7,851,205 B2 12/2010 Kawarada
2007/0207471 A1 9/2007 Osaka et al.

FOREIGN PATENT DOCUMENTS

WO 2009/118475 A2 10/2009
WO 2016/206583 A1 12/2016

OTHER PUBLICATIONS

Fung et al., "Luminescent platinum(II) complexes with functionalized N-heterocyclic carbene or diphosphine selectively probe mismatched and abasic DNA," Nature Communications, Feb., pp. 1-9. (Year: 2016).*

(Continued)

*Primary Examiner* — Young J Kim
(74) *Attorney, Agent, or Firm* — SALIWANCHIK, LLOYD & EISENSCHENK

(57) ABSTRACT

Pertains to the design and applications of platinum (II) compounds supported by a bidentate and N-heterocyclic carbene ligands. The Pt (II) complexes exhibit strong emission intensity differences when contacted with matched and mismatched DNA. In addition, the Pt (II) complexes show a color tunable effect when exposed to mismatched compared to matched DNA, which color effect can be easily detected.

16 Claims, 5 Drawing Sheets

Specification includes a Sequence Listing.

(56) References Cited

OTHER PUBLICATIONS

Solomatina et al., "Cyclometallated platinum(II) complexes containing NHC ligands: synthesis, characterization, photophysics and their application as emitters in OLEDs," Dalton Transactions, vol. 44, pp. 7152-7162. (Year: 2015).*

International Search Report dated Dec. 9, 2020 in International Application No. PCT/CN2020/113745.

Office Action dated May 11, 2023 in Chinese Application No. 202080063210.9.

International Search Report and Written Opinion dated Dec. 9, 2020 in International Application No. PCT/CN2020/113745.

Makarova, A.A. et al., "A curious interplay in the films of N-heterocyclic carbene PtII complexes upon deposition of alkali metals," Scientific Reports, May 6, 2016, 6(25548):1-9.

Graziotto, M.E. et al., "The influence of the ethane-1,2-diamine ligand on the activity of a monofunctional platinum complex," Journal of Inorganic Biochemistry, 2017, 177:328-334.

Okada, T. et al., "Mononuclear Platinum(II) Complex with 2-Phenylpyridine Ligands Showing High Cytotoxicity against Mouse Sarcoma 180 Cells Acquiring High Cisplatin Resistance," Journal of Medicinal Chemistry, 2001, 44(26):4661-4667.

Gabr, M.T. et al., "Platinum(II) Complexes with Sterically Expansive Tetraarylethylene Ligands as Probes for Mismatched DNA," Inorganic Chemistry, 2018, pp. 1-9.

Boynton, A.N, et al., "A Ruthenium(II) Complex as a Luminescent Probe for DNA Mismatches and Abasic Sites," Inorganic Chemistry, 2017, 56:8381-8389.

Boynton, A.N, et al., "[Ru(Me4phen)2dppz"2+, a Light Switch for DNA Mismatches, Journal of the American Chemical Society, 2016, 138:5020-5023.

Nano, A., et al., "A Rhodium-Cyanine Fluorescent Probe: Detection and Signaling of Mismatches in DNA," Journal of the American Chemical Society, 2017, 139:17301-17304.

* cited by examiner

PtCN1

PtCN2

COLOUR TUNABLE LUMINESCENT BIDENTATE PLATINUM (II) COMPLEXES FOR PROBING MISMATCH DNA

CROSS-REFERENCE TO RELATED APPLICATIONS

This application is the U.S. national stage application of International Patent Application No. PCT/CN2020/113745, filed Sep. 7, 2020, which claims the benefit of U.S. Provisional Patent Application No. 62/902,474, filed Sep. 19, 2019, the disclosures of each of which are incorporated herein by reference in their entirety.

REFERENCE TO SEQUENCE LISTING

The Sequence Listing for this application is labeled "SequenceListing.txt" which was created on Oct. 7, 2022 and is 8,192 bytes. The entire content of the sequence listing is incorporated herein by reference in its entirety.

BACKGROUND OF THE INVENTION

The occurrence of errors in DNA poses a threat to human health. DNA mismatches arise as a result of errors in DNA replication and deficiencies in DNA mismatch repair. For example, DNA mismatches are associated with oncogenic transformation and many cancers are characterized by a deficiency in DNA mismatch repair. Thus, the recognition of mismatched DNA is of importance for diagnosis and therapy of various diseases, including cancer.

Current methods used to detect mismatched DNA focus on observing a quantitative change in emission intensity at a wavelength that is similar to the wavelength for matched DNA, which methods have a limited sensitivity and, generally, a low signal-to-noise ratio.

For example, one classical intercalator, ethidium bromide, shows a difference in emission intensity of only 0.9-fold. In order to reliably detect DNA mismatches in cells and tissues, more sensitive methods are needed.

BRIEF SUMMARY OF THE INVENTION

The instant invention provides novel platinum(II) (Pt(II)) complexes that enable to tune the emission wavelength and emission intensity and sensibly differentiate between mismatched and matched DNA. Provided are the design, synthesis, and applications of novel Pt(II) complexes that are useful for the detection of DNA mismatches.

In some embodiments, the Pt(II) complexes of the invention comprise at least one bidentate group and at least one N-heterocyclic carbene group. For example, the (Pt) complexes of the invention comprise the bidentate 2-phenylpyridine and the N-heterocyclic carbene 1-benzyl-3-butylimidazoline (PtCN1).

In other embodiments, the Pt(II) complexes of the invention comprise the bidentate benzo[h]quinolone and the N-heterocylic carbene 1-benzyl-3-butylimidazoline (PtCN2).

Further provided are methods of making and using the Pt(II) complexes of the instant invention. Because the Pt(II) complexes of the invention exhibit a strong emission intensity difference between matched and mismatched DNA, the Pt(II) complexes of the invention can be used to detect DNA mismatches in isolated DNA, cellular DNA and/or in DNA present in tissues.

Further provided are Pt(II) complexes that show a color effect upon interacting with mismatched DNA, which color effect is tunable so as to allow a sensitive differentiation between matched and mismatched DNAs.

Advantageously, the novel Pt(II) complexes can also be used, e.g., in the selective targeting of mismatched DNA. Specifically, the Pt(II) complexes of the invention can be coupled to molecules of interest such as cancer-treating agents and other agents and can be delivered with the Pt(II) complexes of the invention to DNA that contains DNA mismatches.

The use of the Pt(II) complexes of the invention as "scaffolds" for targeted treatment of cells that contain DNA mismatches opens novel treatment modalities based on a cell's or tissues' propensity for DNA mismatches.

BRIEF DESCRIPTION OF THE DRAWINGS

FIG. 1A shows Pt(II)(2-phenylpyridine-1-benzyl-3-butylimidazolium bromide (PtCN1). FIG. 1B shows Pt(II)(benzo[h]quinolone-1-benzyl-3-butylimidazolium bromide (PtCN2).

FIG. 2A shows the emission spectra of PtCN2 in 20 μM Tris buffer after titration with 1-fold CC mismatched DNA. FIG. 2B shows the emission spectra of PtCN2 in 20 μM Tris buffer after titration with 1-fold matched DNA.

FIG. 3A shows the changes in emission intensity of PtCN2 in the presence of mismatched DNA having different nucleotides adjacent to the DNA mismatch. FIG. 3B shows a schematic of the aggregation (left) and de-aggregation (right) of PtCN2 in the absence (left) and presence (right) of mismatched DNA.

FIG. 4A shows the UV-vis absorption of PtCN2 in an aerated $H_2O$/DMSO mixture with increasing DMSO from a $H_2O$/DMSO ratio of 1:9 to a $H_2O$/DMSO ratio of 1:1. FIG. 4B shows the emission spectrum of PtCN2 in pure DMSO compared to a DMSO/$H_2O$ mixture of DMSO:$H_2O$ of 1:1; $\lambda_{ex}$=410 nm.

FIG. 5A shows emission intensity changes of PtCN2 in Tris buffer in the presence of 8 different types of DNA mismatches and 2 types of DNA matches; $\lambda_{ex}$=410 nm. FIG. 5B shows photographs of luminescent color changes of PtCN2 in the presence of mismatched (CC, CA, AT, TC) and matched (CG) DNA under a 365 nm lamp (top) and of PtCN1 in an agarose gel (bottom).

BRIEF DESCRIPTION OF THE SEQUENCES

Figure 1A:
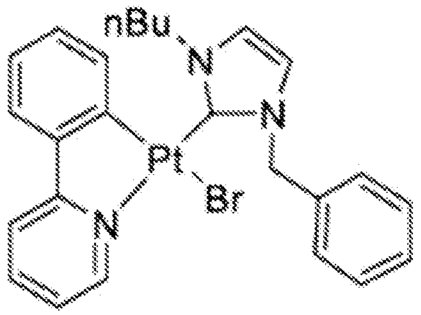
FIGS. 1A and 1B show the structures of two compounds of the instant invention.
Figure 1B:
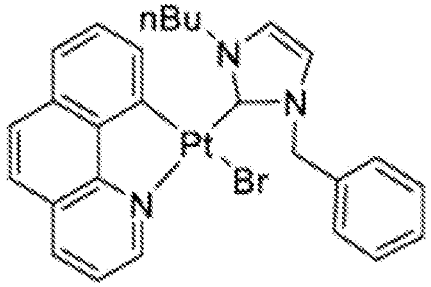

SEQ ID NO: 1 shows the sequence of a hairpin DNA of the invention, wherein N and N' can comprise any of A, T, C, or G.

SEQ ID NO: 2 shows the sequence of a hairpin DNA of the invention comprising an AT match.

SEQ ID NO: 3 shows the sequence of a hairpin DNA of the invention comprising a CG match.

SEQ ID NO: 4 shows the sequence of a hairpin DNA of the invention comprising a CC mismatch.

SEQ ID NO: 5 shows the sequence of a hairpin DNA of the invention comprising an AC mismatch.

SEQ ID NO: 6 shows the sequence of a hairpin DNA of the invention comprising a TC mismatch.

SEQ ID NO: 7 shows the sequence of a hairpin DNA of the invention comprising an AA mismatch.

SEQ ID NO: 8 shows the sequence of a hairpin DNA of the invention comprising a TT mismatch.

SEQ ID NO: 9 shows the sequence of a hairpin DNA of the invention comprising a GA mismatch.

SEQ ID NO: 10 shows the sequence of a hairpin DNA of the invention comprising a GT mismatch.

SEQ ID NO: 11 shows the sequence of a hairpin DNA of the invention comprising a GG mismatch.

SEQ ID NO: 12 shows the sequence of a DNA of the invention.

SEQ ID NO: 13 shows the sequence of a DNA of the invention.

SEQ ID NO: 14 shows the sequence of a DNA of the invention.

SEQ ID NO: 15 shows the sequence of a hairpin DNA of the invention, wherein N and N' are complementary bases and N" and N'" are complementary bases, wherein each of N, N', N", and N'" can be A, T, C, or G.

SEQ ID NO: 16 shows the sequence of a hairpin DNA of the invention, wherein N and N" are A, and N' and N'" are T.

SEQ ID NO: 17 shows the sequence of a hairpin DNA of the invention, wherein N is A, N" is C, N' is T, and N'" is G.

SEQ ID NO: 18 shows the sequence of a hairpin DNA of the invention, wherein N is A, N" is G, N' is T, and N'" is C.

SEQ ID NO: 19 shows the sequence of a hairpin DNA of the invention, wherein N is A, N" is T, N' is T and N'" is A.

SEQ ID NO: 20 shows the sequence of a hairpin DNA of the invention, wherein N is C, N" is A, N' is G, and N'" is T.

SEQ ID NO: 21 shows the sequence of a hairpin DNA of the invention, wherein N is C, N" is C, N' is G, and N'" is G.

SEQ ID NO: 22 shows the sequence of a hairpin DNA of the invention, wherein N is C, N" is G, N' is G, and N'" is C.

SEQ ID NO: 23 shows the sequence of a hairpin DNA of the invention, wherein N is C, N" is T, N' is G, and N'" is A.

SEQ ID NO: 24 shows the sequence of a hairpin DNA of the invention, wherein N is G, N" is A, N' is C, and N'" is T.

SEQ ID NO: 25 shows the sequence of a hairpin DNA of the invention, wherein N is G, N" is C, N' is C, and N'" is G.

SEQ ID NO: 26 shows the sequence of a hairpin DNA of the invention, wherein N is G, N" is G, N' is C, and N'" is C.

SEQ ID NO: 27 shows the sequence of a hairpin DNA of the invention, wherein N is G, N" is T, N' is C, and N'" is A.

SEQ ID NO: 28 shows the sequence of a hairpin DNA of the invention, wherein N is T, N" is A, N' is A, and N'" is T.

SEQ ID NO: 29 shows the sequence of a hairpin DNA of the invention, wherein N is T, N" is C, N' is A, and N'" is G.

SEQ ID NO: 30 shows the sequence of a hairpin DNA of the invention, wherein N is T, N" is G, N' is A, and N'" is C.

SEQ ID NO: 31 shows the sequence of a hairpin DNA of the invention, wherein N is T, N" is T, N' is A, and N'" is A.

SEQ ID NO: 32 shows the sequence of a hairpin DNA of the invention, comprising matched DNA of NCN" and N'GN'".

DETAILED DISCLOSURE OF THE INVENTION

Provided are compounds for selective binding to and detection of DNA mismatches. In some embodiments, the compounds of the invention are platinum(II) (Pt(II)) complexes. In specific embodiments, the Pt(II) complexes of the invention comprise a bidentate and an N-heterocyclic carbene group.

In specific preferred embodiments, the Pt(II) complexes of the invention comprise a bidentate that is 2-phenylpyridine and a N-heterocyclic carbene that is 1-benzyl-3-butylimidazoline (PtCN1). In other specific embodiments, the Pt(II) complexes of the invention comprise a bidentate that is a benzo[h]quinoline and a N-heterocyclic carbene that is 1-benzyl butylimidazoline (PtCN2).

Advantageously, the Pt(II) complexes of the invention preferentially interact with mismatched DNA via cooperative π-stacking and minor groove binding, which interaction can be measured as a change in emission intensity compared to the emission intensity measured of Pt(II) complexes in the presence of matched DNA.

Further provided are methods of making and using the Pt(II) complexes of the instant invention.

The methods of using the Pt(II) complexes of the invention comprise the detection of mismatched DNA in a sample, which sample can be, e.g., an isolated DNA sample, a cell, and/or a tissue sample.

Advantageously, the Pt(II) complexes of the invention exhibit a strong emission intensity difference when contacted with mismatched compared to being contacted with matched DNA.

In some embodiments, the Pt(II) complexes of the instant invention readily identify CC mismatches. In some embodiments, the Pt(II) complexes of the instant invention readily identify CA mismatches. In some embodiments, the Pt(II) complexes of the instant invention readily identify TC mismatches. In some embodiments, the Pt(II) complexes of the instant invention readily identify AA mismatches. In preferred embodiments, the Pt(II) complexes of the invention identify a mismatch when such mismatch is adjacent to a G. In more preferred embodiments, the Pt(II) complexes identify a mismatch when the mismatch follows a G.

In specific embodiments, the Pt(II) complexes of the invention identify DNA mismatches when the nucleotides adjacent to the mismatch are A_A, A_G, C_A, C_G, C_T, T_A, T_C, T_G, or T_T.

In preferred embodiments, the Pt(II) complexes of the invention identify DNA mismatches when the nucleotides adjacent to the mismatch are A_C, _A, G_C, G_G, G_T, or T_C.

For example, when the nucleotides adjacent to a CC mismatch in a DNA are G_T as in 5'- . . . GCT . . . -3', the Pt(II) complexes of the invention show a 6-fold emission intensity increase over a GC matched DNA as in 5'- . . . GGT . . . -3'.

Further, when the nucleotides adjacent to a CC mismatch are G A, G_C, G_G, and A_C as in 5'-, GCA . . . -3', 5'- . . . GCC . . . -3', 5'- . . . GCG . . . -3', and 5'- . . . ACC . . . -3', the Pt(II) complexes of the invention show a 5-fold increase in emission intensity over matched DNA.

Advantageously, the novel Pt(II) complexes allow highly sensitive detection of DNA mismatches. For example, in some embodiments, the Pt(II) complexes of the invention identify mismatches at a ratio of DNA to Pt(II) complex of 2.0. In some embodiments, the Pt(II) complexes of the invention identify mismatches at a ratio of DNA to Pt(II) complex of 1.5. In preferred embodiments, the Pt(II) complexes of the invention identify mismatches at a ratio of DNA to Pt(II) complex of 1. In more preferred embodiments, the Pt(II) complexes of the invention identify mismatches at a ratio of DNA to Pt(II) complex of 0.75. In yet more preferred embodiments, the Pt(II) complexes of the invention identify mismatches at a ratio of DNA to Pt(II) complex of 0.5. In most preferred embodiments, the Pt(II) complexes of the invention identify mismatches at a ratio of DNA to Pt(II) complex of 0.25.

In some embodiments, the Pt(II) complexes of the invention, when in the presence of mismatched DNA, result in distinct bands of emission at wavelengths that are different from the emission wavelengths of the Pt(II) complexes in the presence of matched DNA. In other words, the Pt(II) complexes of the invention do not only increase emission at a similar wavelength when in the presence of mismatched compared to matched DNA but rather induce emission at a different wavelength when in the presence of mismatched compared to matched DNA. This qualitative difference in emission of the Pt(II) complexes of the invention in the presence of mismatched DNA is novel and allows highly sensitive detection of mismatched DNA.

Advantageously, the new emission intensity bands of the Pt(II) complexes in the presence of mismatched compared to matched DNA can be detected as a color shift with the naked eye and, thus, can be used to differentiate between mismatched and matched DNA in a sample by simple visual inspection of the sample under a UV lamp.

Without wanting to be bound by theory it is hypothesized that the Pt(II) complexes of the instant invention when they interact with DNA mismatches de-aggregate, which deaggregation results in an attenuation of low-energy orange emission, an enhancement of high-energy emission around 478 nm and a gradual red shift to 497 nm. The new emission spectrum generated by the Pt(II) complexes interacting with mismatched DNA comprises emission maxima that center at 497 nm and two shoulders on both sides of the maxima. Therefore, when the Pt(II) complexes interact with a mismatch pocket in a DNA molecule, blue-green emission is turned on, which blue-green emission can be discerned with the naked eye under a 365 nm UV lamp from the orange emission obtained with Pt(II) complexes in the presence of matched DNA.

Because the emission spectrum of the Pt(II) complexes of the invention in the aggregation state and the emission spectrum of the Pt(II) complexes in the presence of matched DNA are both different from the emission spectrum of the Pt(II) complexes in the presence of mismatched DNA, the novel Pt(II) complexes allow an easy identification of mismatched DNA in a sample based on the characteristic emission spectrum of Pt(II) complexes and mismatched DNA (new "fingerprint" spectrum).

In contrast, in the presence of matched DNA the Pt(II) complexes of the instant invention show only a small portion of attenuation at low-energy emission and no significant emission enhancement at high-energy emission. Therefore, the novel Pt(II) complexes are sensitive tools with high selectivity for mismatched DNA and low background due to the low interaction with matched DNA. Compared to conventional DNA-binding molecules, the Pt(II) complexes of the invention, therefore, provide an excellent signal-to-noise ratio.

Furthermore, the Pt(II) complexes of the invention not only provide sensitive detection of CC mismatches but also sensitive detection of DNA mismatches including, but not limited to, CA, TC, and AA mismatches. For example, the Pt(II) complexes cause an about 3-fold increase in emission at the characteristic wavelengths (fingerprint spectrum) in the presence of CA and TC hairpin mismatches and an about 2-fold increase in emission at the characteristic wavelengths in the presence of AA hairpin mismatches.

The emission color change from orange in the presence of matched DNA to blue-green in the presence of CA, TC, and AA mismatched DNA can easily be visually observed under a 365 nm UV lamp.

Without wanting to be bound by theory, the increase in emission at the characteristic wavelength between 478 and 497 nm is assumed to be caused by π-stacking of the 2-phenylpyridine and benzo[h]quinoline groups of the Pt(II) complexes of the invention with the mismatched DNA whereas the bulky 1-benzyl-3-butylimidazoline groups provide stabilization of the Pt(II) complex within the minor groove of the DNA molecule.

Furthermore, the different levels of emission intensity changes with different DNA mismatches is thought to be caused by the varying degrees of stability of Pt(II) complexes with the different mismatched DNA and/or different π-stacking interactions of the different nucleotides with the 2-phenylpyridine and benzo[h]quinolone groups of the Pt(II) complexes.

In some specific embodiments of the invention, the Pt(II) complexes comprise a bidentate group and a N-heterocyclic group. Bidentate groups useful in the Pt(II) complexes of the invention include, but are not limited to, 2-phenylpyridine, benzo[h]quinolone, ethylenediamine, 1,2-bis-dimethylphosphinoethane, 1,2-bis-diphenylphosphinoethane, 1,2-bis-dimethylphosphino-methane, dimethoxyethane, 1,2-bis-diphenylphosphinopropane, (S)-BINAP, (R)-BINAP, bipyridyl, phenanthroline, acetate, oxalate, acetylacetonate, beta-diketiminate, catecholate, and glycinate.

In preferred embodiments, the Pt(II) complexes comprise N-heterocyclic groups that are aryl- and/or alkyl-substituted imidazolium groups. In other embodiments, the Pt(II) complexes comprise N-heterocyclic groups that are benzyl- and/or butyl-substituted imidazolium groups.

In further embodiments, the Pt(II) complexes comprise N-heterocyclic groups that are imidazolium groups substituted with at least one alkyl group, at least one aryl group, at least one anthracene, at least one phenanthrene groups, and/or combinations thereof.

Other N-heterocyclic groups useful in the Pt(II) complexes of the invention include, but are not limited to, alkyl- and/or aryl-substituted imidazoline groups, 1,3-bis(2,4,6-trimethylphenyl)-imidazolium (IMes), 1,3-bis(2,4,6-trimethylphenyl)-4,5-dihydroimidazol-2-ylidene (SIMes), 1,3-bis(2,6-diisopropylphenyl)imidazol-2-ylidene (IPr), 1,3-bis(2,6-diisopropylphenyl)imidazolidin-2-ylidene (SIPr), 1,3-bis(2,6-diisopropylphenyl)imidazolium-2-carboxylate, 2-chloro-1,3-bis(2,6-diisopropylphenyl)-1H-imidazolium chloride, 2-chloro-1,3-dimethylimidazolinium tetrafluoroborate, 1,3-dimesitylimidazol-2-ylidene, 1,3-di-tert-butylimidazol-2-ylidene, 1,3-di(1-adamantyl)imidazolinium tetrafluoroborate, 1,3-dicyclohexylimidazolium tetrafluoroborate, 1,4-dimethyl-1,2,4-triazolium iodide, 6,7-dihydro-2-pentafluorophenyl-5H-pyrrolo[2,1-c][1,2,4]triazolium tetrafluoroborate, 1,3-dimethylimidazolium-2-carboxylate, 1-(2,6-diethylphenyl)-2,2,4-trimethyl-4-phenyl-3,4-dihydro-2H-pyrrol-1-ium tetrafluoroborate, 3,3'-methylenebis(1-tert-butyl-3-imidazolium bromide), 3,3'-methylenebis[1-(2,6-diisopropylphenyl)-3-imidazolium bromide], 1-methyl-3-propylimidazolium tetrafluoroborate, and 1,1'-(2,6-pyridinediyl)bis(3-methylimidazolium) dibromide.

Using the techniques disclosed in the instant invention, a person can use routine experimentation to substitute a bidentate and/or a N-heterocyclic group in the Pt(II) complexes of the invention to obtain additional Pt(II) complexes of the invention.

Further methods of using the Pt(II) complexes in the invention are provided. In some embodiments, a method for quantifying DNA mismatches in a sample is provided, the method comprising: providing a sample suspected to comprise DNA mismatches and digesting the DNA in the sample with restriction enzymes to obtain DNA molecules comprising between 20 and 200 nucleotides; providing a sample comprising matched DNA molecules comprising between 20 and 200 nucleotides; contacting the samples with a concentration of a Pt(II) complex according to claim 1 such that the ratio of DNA molecules to Pt(II) complex is at least 1; measuring emission spectra of the samples after contacting them with the Pt(II) complex; quantifying the orange-red and blue-green emission intensities in the emission spectra; and quantifying the number of DNA mismatches in the sample suspected to comprise DNA mismatches based on the orange-red and blue-green emission intensity of the sample; wherein the blue-green emission intensity is equal to or less than the orange-red intensity in the sample of matched DNA molecules; wherein a blue-green emission intensity that is greater than the orange-red intensity indicates the presence of DNA mismatches in the sample suspected to comprise DNA mismatches; and wherein the blue-green emission intensity is proportional to the number of DNA mismatches in the DNA molecules of said sample.

In other embodiments, a method is provided for quantifying DNA mismatches in a sample, the method comprising: providing a sample suspected to comprise DNA mismatches and digesting the DNA in the sample with restriction enzymes to obtain DNA molecules comprising between 20 and 200 nucleotides; providing a sample comprising matched DNA molecules comprising between 20 and 200 nucleotides; contacting the samples with a concentration of a Pt(II) complex according to claim 1 such that the ratio of DNA molecules to Pt(II) complex is at least 1; contacting the samples with UV light; and determining the color of the sample; wherein an orange color indicates an absence of DNA mismatches, and a blue-green color indicates the presence of DNA mismatches; wherein the intensity of the blue-green color in the sample is proportional to the number of DNA mismatches in the DNA molecules.

The length of the DNA molecules useful in the methods of the invention can be between 5 nucleotides and 1000 nucleotides and any length therebetween. Restriction endonucleases that digest DNA including, but not limited to, genomic DNA and plasmid DNA to fragments of between 5 nucleotides and 1000 nucleotides are known in the art. Specific endonucleases can be chosen by the skilled artisan to digest DNA in a sample to desired lengths of DNA molecules within the range of 5 to 1000 nucleotides. In preferred embodiments, the restriction enzymes are used that digest DNA to fragments between about 5 to about 500 nucleotides, between about 10 to about 400 nucleotides, between about 15 to about 300 nucleotides, or between about 20 to about 200 nucleotides.

EXAMPLES

Example 1—Synthesis and Characterization of Novel Pt(II) Complexes

[Pt(C^N)(μ-Cl)]$_2$ (HC^N=2-phenylpyridine; benzo[h]quinoline) and 1-benzyl-3-butylimidazolium bromide were synthesized according to reported procedures.

For PtCN1, a mixture of [Pt(C^N)(μ-Cl)]2 (77.7 mg, 0.101 mmol), where HC^N=2-phenylpyridine, 1-benzyl-3-butylimidazolium bromide (29.8 mg, 0.101 mmol), sodium acetate (16.6 mg, 0.202 mmol), and sodium bromide (20.8 mg, 0.202 mmol) were heated at 100° C. in a DMSO solution for overnight. Then DMSO was evaporated under reduced pressure to 3 to 5 ml and an amount of water was added to afford the precipitate. The product was purified by column chromatography on $SiO_2$ by using a mixture of hexane and dichloromethane as eluent. Recrystallization was performed on slow evaporation on hexane and dichloromethane mixture.

The solid was collected and redissolved in acetonitrile, then it was slowly evaporated overnight. The product was further dissolved in a small amount of acetone and a saturated sodium bromide aqueous solution was added to fully obtain the bromide subsistent product, then washed with water and $Et_2O$.

For PtCN2, where HC^N=benzo[h]quinoline, a similar procedure as described above for PtCN1 was employed; however, benzo[h]quinoline was used instead of 2-phenylpyridine.

Example 2—Detection of Emission Spectra for Cc Mismatched and Matched DNA

Figure 2A:
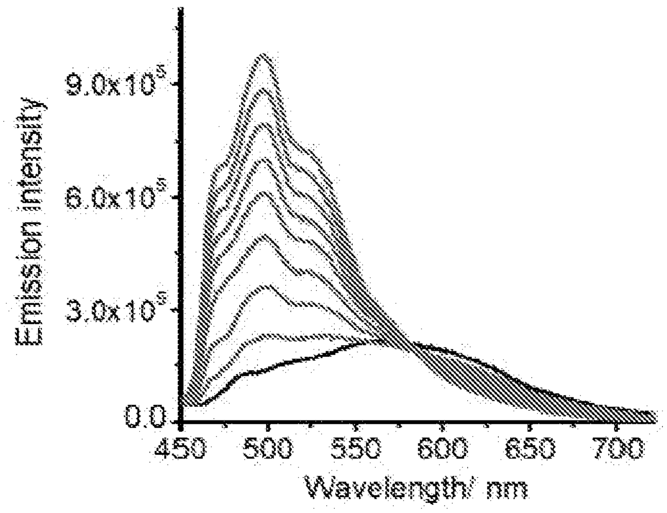
FIGS. 2A and 2B show the emission spectra of PtCN2 in the presence of mismatched and matched DNA.
Figure 2B:
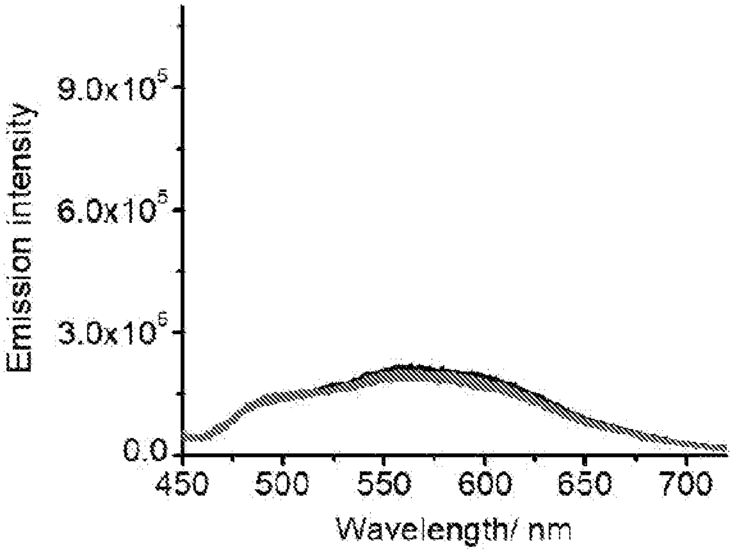

The emission spectra for detection of CC mismatched DNA and matched DNA were determined (FIGS. 2A and 2B). The emission spectra of PtCN2 (20 μM) in a Tris buffer solution (5 mM Tris-HCl and 50 mM NaCl, pH 7.1) were measured after titration with 1-fold CC mismatched DNA or match DNA. When the Pt(II) complex interacted with a CC hairpin mismatch (e.g., SEQ ID NO: 4), the de-aggregation of Pt(II) complexes resulted in an attenuation of low-energy orange emission and an enhancement of high-energy emission around 478 nm which was gradually red shifted to 497 nm. A new emission spectrum (fingerprint spectrum for Pt(II) complexes in the presence of mismatched DNA) emerged with emission maxima centering at 497 nm and two shoulders on the both sides. Thus, upon Pt(II) complex interaction with mismatched DNA blue-green emission was turned on. The Pt(II)-mismatch DNA spectrum was different from the emission spectrum of aggregated Pt(II) complex and Pt(II) complex in a panel of degassed organic solvents. For the cognate matched DNA (e.g. SEQ ID NO: 3), only a small portion of attenuation at low-energy emission was observed and no significant emission enhancement at high-energy emission. Therefore, the novel Pt(II) complexes provided a new fingerprint spectrum, which easily identified the CC mismatch DNA.

Example 3—Emission Enhancement of Ptcn2

Figure 3A:
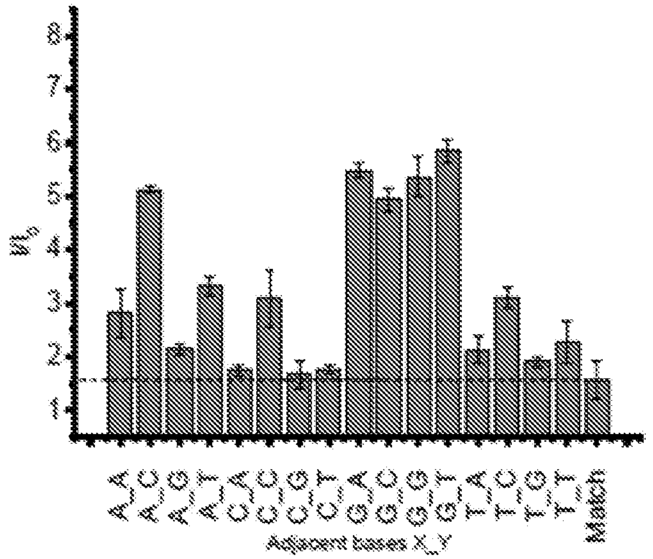
FIGS. 3A and 3B show the mechanism of specific binding of Pt(II) complexes of the invention to mismatched DNA and the effect of adjacent bases.

Emission enhancement of PtCN2 was determined in the presence of mismatched DNA with different adjacent base pairs and cognate match DNA at a ratio of Pt(II) complex to DNA of 1.0 (FIG. 3A). The emission response of PtCN2 towards DNA harboring CC mismatches with different adjacent base pairs was examined at 497 nm. Most hairpin CC mismatched DNA showed higher emission intensity compared to matched DNA. Especially, the 5'- . . . GCT . . . -3' (SEQ ID NO: 27) displayed a 6-fold higher emission response at 497 nm than matched DNA (SEQ ID NO: 32) and 5'- . . . GCA . . . -3' (SEQ ID NO: 24), 5'- . . . GCC . . . -3' (SEQ ID NO: 25), GCG . . . -3' (SEQ ID NO: 26) and 5'- . . . ACC . . . -3' (SEQ ID NO: 17) showed 5-fold higher emission intensities over matched DNA.

Figure 3B:
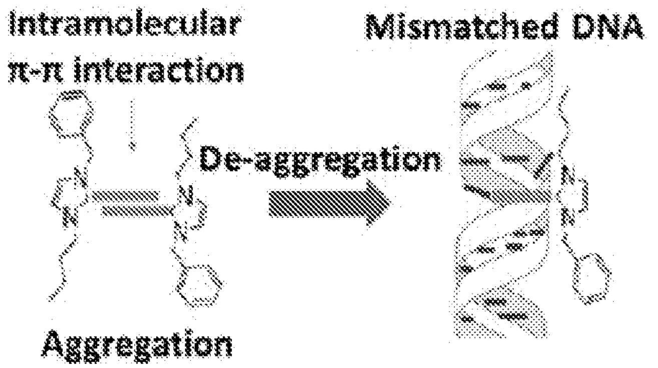

The mechanism of Pt(II) complex aggregation and de-aggregation in the presence of mismatched DNA (FIG. 3B) is thought to be caused by π-π interaction between two Pt(II) molecules of the invention where the π-π stacking moiety is, e.g., benzo[h]quinoline (FIG. 3B, green bars) and the DNA minor groove binding moiety is, e.g., benzyl-butyl-imidazoline.

Example 4—Uv-Vis Absorption in Aerated $H_2O$/Dmso

Figure 4A:
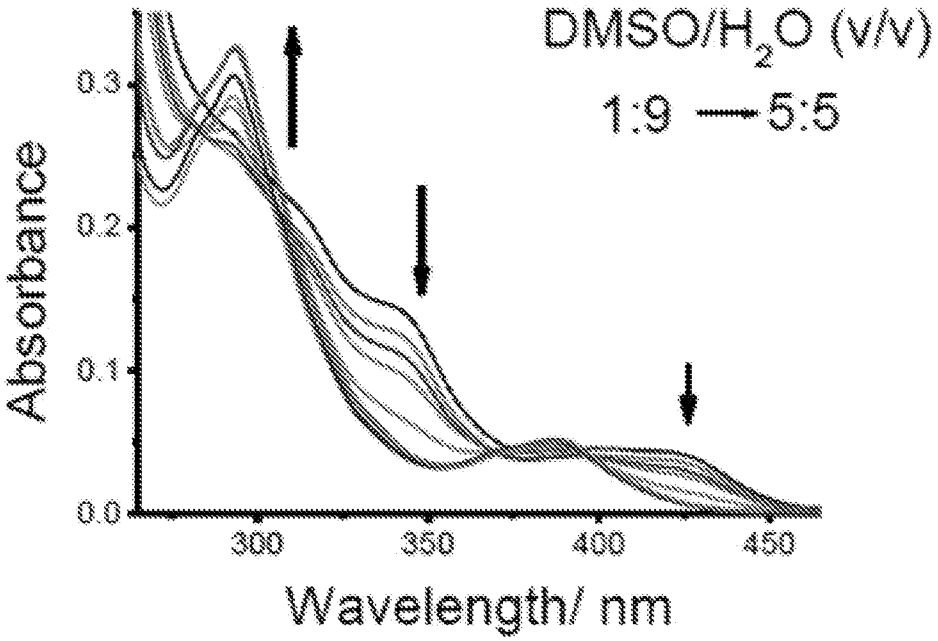
FIGS. 4A and 4B show the UV-vis absorption of PtCN2 in different aerated mixtures of DMSO/$H_2O$.
Figure 4B:
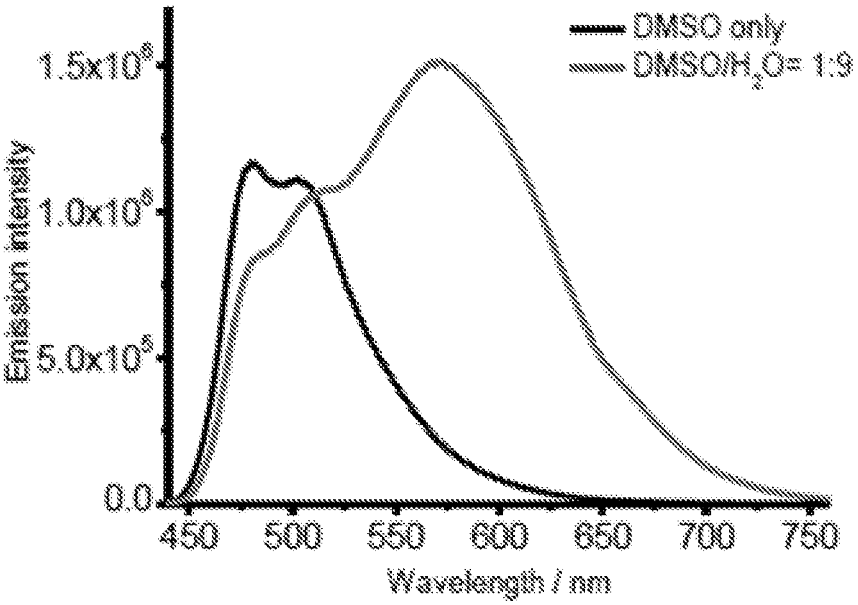

The UV-vis absorption of PtCN2 ($2\times10^{-5}$ M) in the presence of hairpin mismatched DNA (SEQ ID NO: 4) and matched DNA (SEQ ID NO: 2) in aerated $H_2O$/DMSO mixture was measured upon increasing the DMSO ratio from 1:9 to 1:1 (v/v) (FIG. 4A). An increase in DMSO resulted in an increase in high-energy absorption and two decreases in lower energy UV-vis absorption. Further, emission spectra of PtCN2 ($4\times10^{-5}$ M) in the presence of hairpin mismatched DNA (SEQ ID NO: 4) and matched DNA (SEQ ID NO:2) measured in DMSO only and in DMSO/$H_2O$ at a ratio of 1:9 (v/v) showed an emission intensity increase at high-energy wavelengths when the Pt(II) complex of the invention was in the presence of pure DMSO compared to low-energy emission when the Pt(II) complex was present in a DMSO/water mixture of 1:9 (FIG. 4B).

Figure 5A:
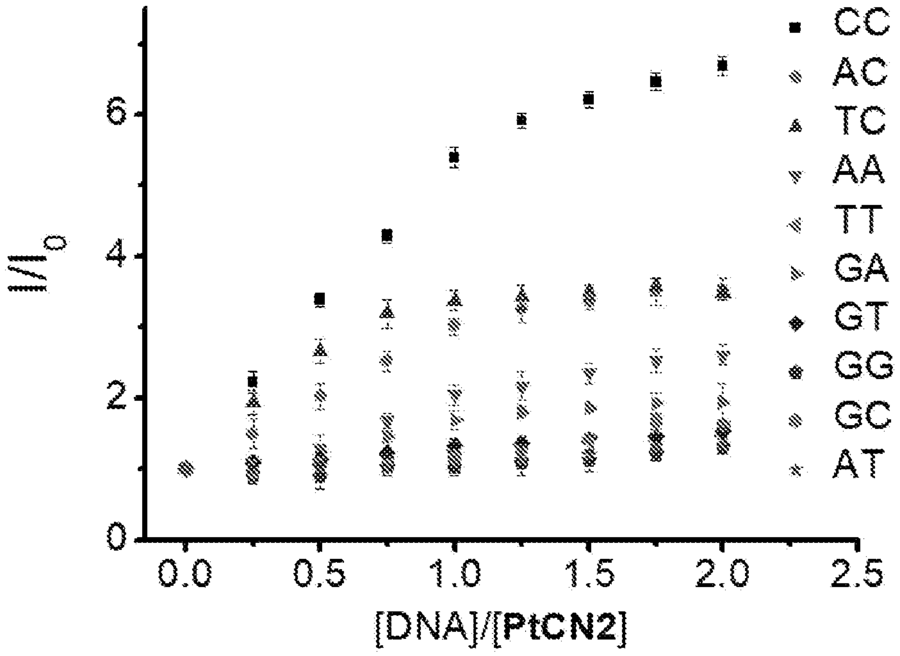
FIGS. 5A and 5B show emission intensity changes of a Pt(II) complex of the invention in the presence of different types of DNA mismatches.

Example 5—Emission Intensity Changes of Ptcn2 with Different Types of Mismatched DNA Emission intensity changes of PtCN2 (20 μM) in a Tris buffer solution were measured during titration with different types of mismatched DNA at $\lambda_{ex}$=410 nm. Surprisingly, increased emission intensity at the high-energy fingerprint spectrum of Pt(II) complexes interacting with mismatched DNA were observed not only for CC mismatches (SEQ ID NO: 4) but also for other DMA mismatches. The emission increased around 3-fold for CA (SEQ ID NO: 5) and TC hairpin mismatched DNA (SEQ ID NO: 6), and 2-fold for AA hairpin mismatched DNA (SEQ ID NO: 7) (FIG. 5A).

Figure 5B:
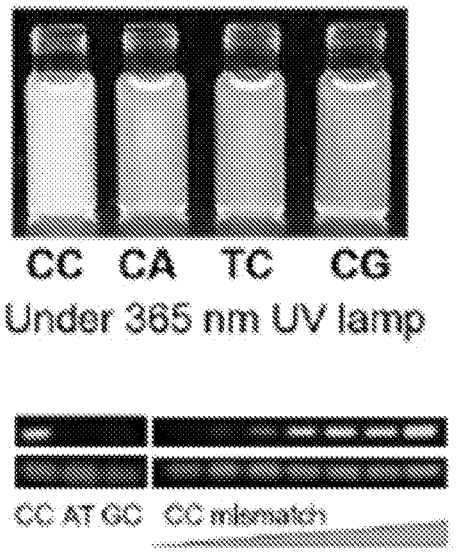

Photographs under UV light of solutions of Pt(II) complexes with CC, CA, and TC mismatched DNA compared to CG matched DNA showed luminescent color changes from orange for CG-matched DNA to pale green for CA and TC mismatched DNAs to bright blue-green for CC mismatched DNA (FIG. 5B).

These significant color changes caused by emission wavelength changes in the presence of different mismatched DNAs suggest that different types of mismatched DNA have a varying degree of stability with Pt(II) complexes of the invention.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for quantifying DNA mismatches in a sample, the method comprising: providing a sample suspected to comprise DNA mismatches and digesting the DNA in the sample with restriction enzymes to obtain DNA molecules comprising between 20 and 200 nucleotides;

providing a sample of matched DNA molecules comprising between 20 and 200 nucleotides;

contacting the samples with a concentration of a Pt (II) complex comprising a bidentate group, a halogen group, and a N-heterocyclic group, wherein the N-heterocyclic group further comprises a hetero substituted imidazolium group such that the ratio of DNA molecules to Pt (II) complex is at least 1;

measuring emission spectra of the samples after contacting them with the Pt (II) complex;

quantifying the orange-red and blue-green emission intensities in the emission spectra; and quantifying the number of DNA mismatches in the sample suspected to comprise DNA mismatches based on the orange-red and blue-green emission intensity of the sample;

wherein the blue-green emission intensity is equal to or less than the orange-red intensity in the sample of matched DNA molecules;

wherein a blue-green emission intensity that is greater than the orange-red intensity indicates the presence of DNA mismatches in the sample suspected to comprise DNA mismatches; and wherein the blue-green emission intensity is proportional to the number of DNA mismatches in the DNA molecules of the sample suspected to comprise DNA mismatches.

2. The method of claim 1, wherein the bidentate group is selected from 2-phenylpyridine and benzo[h]quinoline.

3. The method of claim 1, wherein the imidazolium group is substituted with at least one alkyl-, at least one aryl-, at least one phosphino-, and/or at least one adamantyl group.

4. The method of claim 1, wherein the imidazolium group is substituted with at least one alkyl group.

5. The method of claim 1, wherein the imidazolium group is substituted with at least one aryl group.

6. The method of claim 1, wherein the imidazolium group is substituted with at least one alkyl group and at least one aryl group.

7. The method of claim 6, wherein the alkyl group is a butyl group.

8. The method of claim 1, wherein the halogen group is bromide or chloride.

9. A method for quantifying DNA mismatches in a sample, the method comprising:

providing a sample suspected to comprise DNA mismatches and digesting the DNA in the sample with restriction enzymes to obtain DNA molecules comprising between 20 and 200 nucleotides;

providing a sample comprising matched DNA molecules comprising between 20 and 200 nucleotides;

contacting the samples with a concentration of a Pt (II) complex comprising a bidentate group, a halogen group, and a N-heterocyclic group, wherein the N-heterocyclic group further comprises a hetero substituted imidazolium group such that the ratio of DNA molecules to Pt (II) complex is at least 1;

contacting the samples with UV light; and determining the color of the sample; wherein the color of the sample is orange in the sample comprising matched DNA molecules; and a blue-green color in the sample suspected to comprise DNA mismatches indicates the presence of DNA mismatches; wherein the intensity of the blue-green color in the sample suspected to comprise DNA mismatches is proportional to the number of DNA mismatches in the DNA molecules of said sample.

10. The method of claim 9, wherein the bidentate group is selected from 2-phenylpyridine and benzo[h]quinoline.

11. The method of claim 9, wherein the imidazolium group is substituted with at least one alkyl-, at least one aryl-, at least one phosphino-, and/or at least one adamantyl group.

12. The method of claim 9, wherein the imidazolium group is substituted with at least one alkyl group.

13. The method of claim 9, wherein the imidazolium group is substituted with at least one aryl group.

14. The method of claim 9, wherein the imidazolium group is substituted with at least one alkyl group and at least one aryl group.

15. The method of claim 14, wherein the alkyl group is a butyl group.

16. The method of claim 9, wherein the halogen group is bromide or chloride.

* * * * *

SEQUENCE LISTING

<160> NUMBER OF SEQ ID NOS: 32

<210> SEQ ID NO 1
<211> LENGTH: 29
<212> TYPE: DNA
<213> ORGANISM: Artificial Sequence
<220> FEATURE:
<223> OTHER INFORMATION: Hairpin DNA
<220> FEATURE:
<221> NAME/KEY: misc_feature
<222> LOCATION: (7)..(7)
<223> OTHER INFORMATION: N variable nucleotide - can be A, T, C, or G
<220> FEATURE:
<221> NAME/KEY: misc_feature
<222> LOCATION: (23)..(23)
<223> OTHER INFORMATION: N' variable nucleotide - can be A, T, C, or G

<400> SEQUENCE: 1
ggcaggnatg gctttttgcc atncctgcc 29

<210> SEQ ID NO 2
<211> LENGTH: 29
<212> TYPE: DNA
<213> ORGANISM: Artificial Sequence
<220> FEATURE:
<223> OTHER INFORMATION: Hairpin DNA

<400> SEQUENCE: 2
ggcaggaatg gctttttgcc attcctgcc 29

<210> SEQ ID NO 3
<211> LENGTH: 29
<212> TYPE: DNA
<213> ORGANISM: Artificial Sequence
<220> FEATURE:
<223> OTHER INFORMATION: Hairpin DNA

<400> SEQUENCE: 3
ggcaggcatg gctttttgcc atgcctgcc 29

<210> SEQ ID NO 4
<211> LENGTH: 29
<212> TYPE: DNA
<213> ORGANISM: Artificial Sequence
<220> FEATURE:
<223> OTHER INFORMATION: Hairpin DNA

<400> SEQUENCE: 4
ggcaggcatg gctttttgcc atccctgcc 29

<210> SEQ ID NO 5
<211> LENGTH: 29
<212> TYPE: DNA
<213> ORGANISM: Artificial Sequence
<220> FEATURE:
<223> OTHER INFORMATION: Hairpin DNA

<400> SEQUENCE: 5
ggcaggaatg gctttttgcc atccctgcc 29

<210> SEQ ID NO 6
<211> LENGTH: 29
<212> TYPE: DNA
<213> ORGANISM: Artificial Sequence
<220> FEATURE:
<223> OTHER INFORMATION: Hairpin DNA

<400> SEQUENCE: 6
ggcaggtatg gctttttgcc atccctgcc 29

<210> SEQ ID NO 7
<211> LENGTH: 29
<212> TYPE: DNA
<213> ORGANISM: Artificial Sequence
<220> FEATURE:
<223> OTHER INFORMATION: Hairpin DNA

<400> SEQUENCE: 7
ggcaggaatg gctttttgcc atacctgcc 29

<210> SEQ ID NO 8
<211> LENGTH: 29
<212> TYPE: DNA
<213> ORGANISM: Artificial Sequence
<220> FEATURE:
<223> OTHER INFORMATION: Hairpin DNA

<400> SEQUENCE: 8
ggcaggtatg gctttttgcc attcctgcc 29

<210> SEQ ID NO 9
<211> LENGTH: 29
<212> TYPE: DNA
<213> ORGANISM: Artificial Sequence
<220> FEATURE:
<223> OTHER INFORMATION: Hairpin DNA

<400> SEQUENCE: 9
ggcagggatg gctttttgcc atacctgcc 29

<210> SEQ ID NO 10
<211> LENGTH: 29
<212> TYPE: DNA
<213> ORGANISM: Artificial Sequence
<220> FEATURE:
<223> OTHER INFORMATION: Hairpin DNA

<400> SEQUENCE: 10
ggcagggatg gctttttgcc attcctgcc 29

<210> SEQ ID NO 11
<211> LENGTH: 29
<212> TYPE: DNA
<213> ORGANISM: Artificial Sequence
<220> FEATURE:
<223> OTHER INFORMATION: Hairpin DNA

<400> SEQUENCE: 11
ggcagggatg gctttttgcc atgcctgcc 29

<210> SEQ ID NO 12
<211> LENGTH: 17
<212> TYPE: DNA
<213> ORGANISM: Artificial Sequence
<220> FEATURE:
<223> OTHER INFORMATION: Double Strand DNA

<400> SEQUENCE: 12
gcgccgtcgt ccatgtg 17

<210> SEQ ID NO 13
<211> LENGTH: 17
<212> TYPE: DNA
<213> ORGANISM: Artificial Sequence
<220> FEATURE:
<223> OTHER INFORMATION: Double Strand DNA

<400> SEQUENCE: 13
cacatggacg acggcgc 17

<210> SEQ ID NO 14
<211> LENGTH: 17
<212> TYPE: DNA
<213> ORGANISM: Artificial Sequence
<220> FEATURE:
<223> OTHER INFORMATION: Double Strand DNA

<400> SEQUENCE: 14
cacatgcacg acggcgc 17

<210> SEQ ID NO 15
<211> LENGTH: 29
<212> TYPE: DNA
<213> ORGANISM: Artificial Sequence
<220> FEATURE:
<223> OTHER INFORMATION: Hairpin DNA
<220> FEATURE:
<221> NAME/KEY: misc_feature
<222> LOCATION: (6)..(6)
<223> OTHER INFORMATION: N" variable nucleotide - can be A, T, C, or G
<220> FEATURE:

<221> NAME/KEY: misc_feature
<222> LOCATION: (8)..(8)
<223> OTHER INFORMATION: N variable nucleotide - can be A, T, C, or G
<220> FEATURE:
<221> NAME/KEY: misc_feature
<222> LOCATION: (22)..(22)
<223> OTHER INFORMATION: N' variable nucleotide - can be A, T, C, or G
<220> FEATURE:
<221> NAME/KEY: misc_feature
<222> LOCATION: (24)..(24)
<223> OTHER INFORMATION: N'" variable nucleotide - can be A, T, C, or G

<400> SEQUENCE: 15
ggcagncntg gctttttgcc ancnctgcc 29

<210> SEQ ID NO 16
<211> LENGTH: 29
<212> TYPE: DNA
<213> ORGANISM: Artificial Sequence
<220> FEATURE:
<223> OTHER INFORMATION: Hairpin DNA

<400> SEQUENCE: 16
ggcagacatg gctttttgcc atctctgcc 29

<210> SEQ ID NO 17
<211> LENGTH: 29
<212> TYPE: DNA
<213> ORGANISM: Artificial Sequence
<220> FEATURE:
<223> OTHER INFORMATION: Hairpin DNA

<400> SEQUENCE: 17
ggcagccatg gctttttgcc atcgctgcc 29

<210> SEQ ID NO 18
<211> LENGTH: 29
<212> TYPE: DNA
<213> ORGANISM: Artificial Sequence
<220> FEATURE:
<223> OTHER INFORMATION: Hairpin DNA

<400> SEQUENCE: 18
ggcaggcatg gctttttgcc atccctgcc 29

<210> SEQ ID NO 19
<211> LENGTH: 29
<212> TYPE: DNA
<213> ORGANISM: Artificial Sequence
<220> FEATURE:
<223> OTHER INFORMATION: Hairpin DNA

<400> SEQUENCE: 19
ggcagtcatg gctttttgcc atcactgcc 29

<210> SEQ ID NO 20
<211> LENGTH: 29
<212> TYPE: DNA
<213> ORGANISM: Artificial Sequence
<220> FEATURE:
<223> OTHER INFORMATION: Hairpin DNA

<400> SEQUENCE: 20
ggcagacctg gctttttgcc agctctgcc 29

<210> SEQ ID NO 21
<211> LENGTH: 29

<212> TYPE: DNA
<213> ORGANISM: Artificial Sequence
<220> FEATURE:
<223> OTHER INFORMATION: Hairpin DNA

<400> SEQUENCE: 21
ggcagccctg gctttttgcc agcgctgcc 29

<210> SEQ ID NO 22
<211> LENGTH: 29
<212> TYPE: DNA
<213> ORGANISM: Artificial Sequence
<220> FEATURE:
<223> OTHER INFORMATION: Hairpin DNA

<400> SEQUENCE: 22
ggcaggcctg gctttttgcc agccctgcc 29

<210> SEQ ID NO 23
<211> LENGTH: 29
<212> TYPE: DNA
<213> ORGANISM: Artificial Sequence
<220> FEATURE:
<223> OTHER INFORMATION: Hairpin DNA

<400> SEQUENCE: 23
ggcagtcctg gctttttgcc agcactgcc 29

<210> SEQ ID NO 24
<211> LENGTH: 29
<212> TYPE: DNA
<213> ORGANISM: Artificial Sequence
<220> FEATURE:
<223> OTHER INFORMATION: Hairpin DNA

<400> SEQUENCE: 24
ggcagacgtg gctttttgcc acctctgcc 29

<210> SEQ ID NO 25
<211> LENGTH: 29
<212> TYPE: DNA
<213> ORGANISM: Artificial Sequence
<220> FEATURE:
<223> OTHER INFORMATION: Hairpin DNA

<400> SEQUENCE: 25
ggcagccgtg gctttttgcc accgctgcc 29

<210> SEQ ID NO 26
<211> LENGTH: 29
<212> TYPE: DNA
<213> ORGANISM: Artificial Sequence
<220> FEATURE:
<223> OTHER INFORMATION: Hairpin DNA

<400> SEQUENCE: 26
ggcaggcgtg gctttttgcc acccctgcc 29

<210> SEQ ID NO 27
<211> LENGTH: 29
<212> TYPE: DNA
<213> ORGANISM: Artificial Sequence
<220> FEATURE:
<223> OTHER INFORMATION: Hairpin DNA

<400> SEQUENCE: 27
ggcagtcgtg gctttttgcc accactgcc 29

<210> SEQ ID NO 28
<211> LENGTH: 29
<212> TYPE: DNA
<213> ORGANISM: Artificial Sequence
<220> FEATURE:
<223> OTHER INFORMATION: Hairpin DNA

<400> SEQUENCE: 28
ggcagacttg gctttttgcc aactctgcc 29

<210> SEQ ID NO 29
<211> LENGTH: 29
<212> TYPE: DNA
<213> ORGANISM: Artificial Sequence
<220> FEATURE:
<223> OTHER INFORMATION: Hairpin DNA

<400> SEQUENCE: 29
ggcagccttg gctttttgcc aacgctgcc 29

<210> SEQ ID NO 30
<211> LENGTH: 29
<212> TYPE: DNA
<213> ORGANISM: Artificial Sequence
<220> FEATURE:
<223> OTHER INFORMATION: Hairpin DNA

<400> SEQUENCE: 30
ggcaggcttg gctttttgcc aaccctgcc 29

<210> SEQ ID NO 31
<211> LENGTH: 29
<212> TYPE: DNA
<213> ORGANISM: Artificial Sequence
<220> FEATURE:
<223> OTHER INFORMATION: Hairpin DNA

<400> SEQUENCE: 31
ggcagtcttg gctttttgcc aacactgcc 29

<210> SEQ ID NO 32
<211> LENGTH: 29
<212> TYPE: DNA
<213> ORGANISM: Artificial Sequence
<220> FEATURE:
<223> OTHER INFORMATION: Hairpin DNA
<220> FEATURE:
<221> NAME/KEY: misc_feature
<222> LOCATION: (6)..(6)
<223> OTHER INFORMATION: N" variable nucleotide - can be A, T, C, or G
<220> FEATURE:
<221> NAME/KEY: misc_feature
<222> LOCATION: (8)..(8)
<223> OTHER INFORMATION: N variable nucleotide - can be A, T, C, or G
<220> FEATURE:
<221> NAME/KEY: misc_feature
<222> LOCATION: (22)..(22)
<223> OTHER INFORMATION: N' variable nucleotide - can be A, T, C, or G
<220> FEATURE:
<221> NAME/KEY: misc_feature
<222> LOCATION: (24)..(24)
<223> OTHER INFORMATION: N'" variable nucleotide - can be A, T, C, or G

<400> SEQUENCE: 32
ggcagnchtg gctttttgcc angnctgcc 29